United States Patent [19]

Sheinkop Isac

[11] Patent Number: 4,877,436
[45] Date of Patent: Oct. 31, 1989

[54] CONTINUOUS VISCOSITY MONITORING OF GLASS

[76] Inventor: Sheinkop Isac, 19513-M Gunners Branch Rd., Germantown, Md. 20874

[21] Appl. No.: 322,211

[22] Filed: Mar. 13, 1989

[51] Int. Cl.$^4$ .............................................. C03B 5/24
[52] U.S. Cl. ........................................... 65/29; 65/2; 65/11.1; 65/158; 65/160; 65/164
[58] Field of Search ...................... 65/2, 11.1, 29, 158, 65/160, 162, 163, 164

[56] References Cited

U.S. PATENT DOCUMENTS

| | | | |
|---|---|---|---|
| 4,046,536 | 9/1977 | Smithgall | 65/2 |
| 4,090,241 | 5/1978 | Houston | 65/2 |
| 4,205,973 | 6/1980 | Ryan | 65/29 |
| 4,280,827 | 7/1981 | Murphy et al. | 65/2 X |
| 4,363,827 | 12/1982 | Eichenbaum | 65/29 X |
| 4,541,856 | 9/1985 | Maillard et al. | 65/158 X |

Primary Examiner—Arthur Kellogg

[57] ABSTRACT

A method for manufacturing glass comprises forming glass from molten mineral material, continuously discharging an auxiliary stream of molten mineral material, continuously measuring the temperature and the mass flow rate by laser means of the auxiliary stream, calculating the viscosity of the material using the measured mass flow rate and modifying a process parameter in response to the measured temperature and calculated viscosity of the auxiliary stream. The laser means is also disclosed.

7 Claims, 3 Drawing Sheets

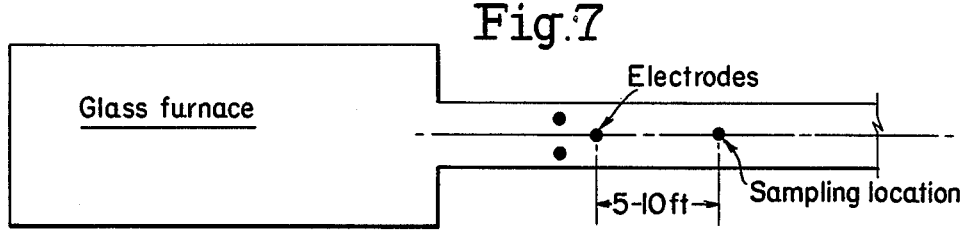
Fig. 7
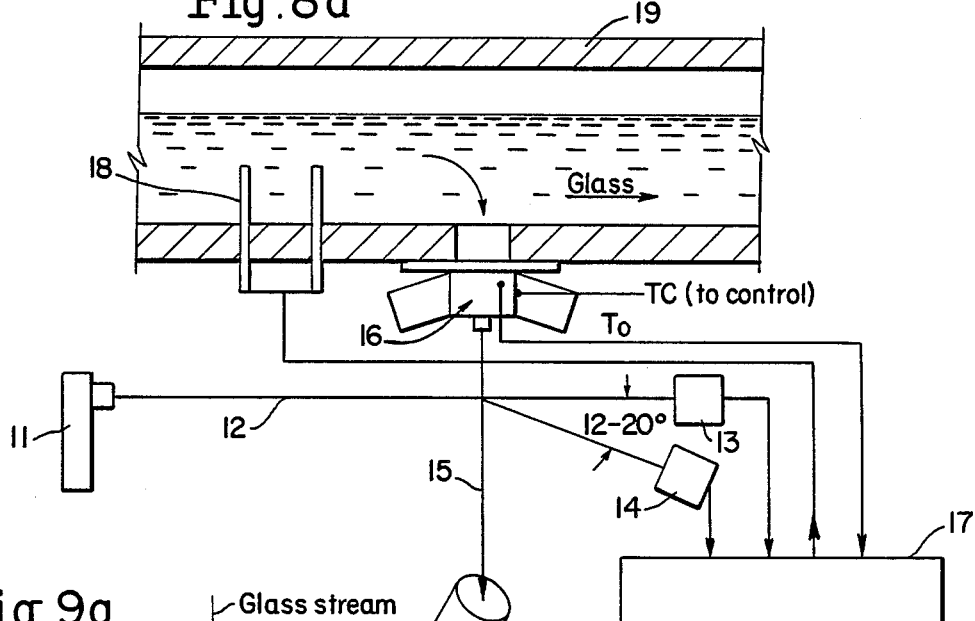
Fig. 8a
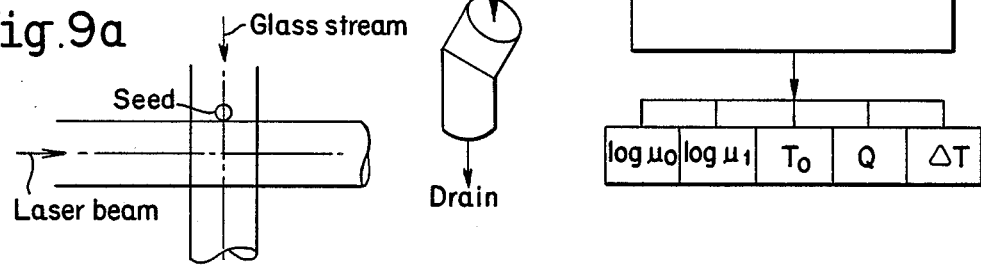
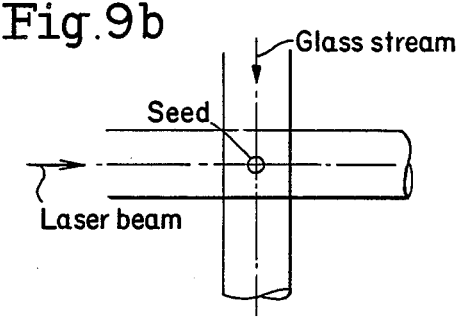
Fig. 9a
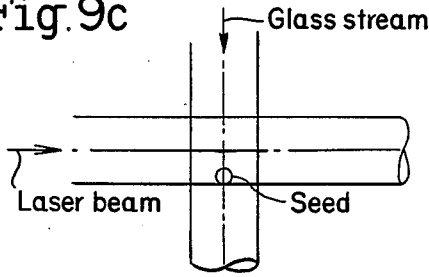
Fig. 9b
Fig. 9c
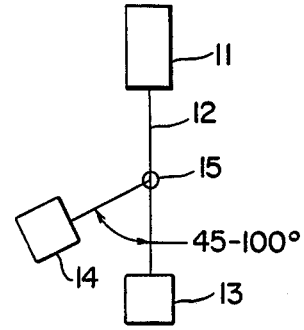
Fig. 8b

CONTINUOUS VISCOSITY MONITORING OF GLASS

BACKGROUND OF THE INVENTION

1. Field of the Invention

This invention pertains to manufacturing glass products from molten mineral material. More particularly, this invention pertains to controlling the flow and viscosity of molten glass during production.

2. Description of the Background Art

It is a common practice to manufacture glass by supplying molten mineral material from a furnace or melter to a glass forming apparatus. One of the problems which has long plagued the manufacturers of glass is the variation in the viscosity of the glass flowing into the glass forming apparatus. In a continuous glass manufacturing process, variations in the viscosity of the glass can adversely affect the consistency and quality of the end product.

Existing methods of glass viscosity measurement are not sufficient for adequate control. Typically, a glass sample is taken from the furnace or forehearth and the sample is removed to a testing station where the viscosity is determined using calibrated instruments. The process takes a considerable amount of time, and is done off line. The results of the viscosity analysis are often learned too late to make any correction in the fiber forming process.

Chrisman in U.S. Pat. No. 4,277,274, discloses a method of controlling a glass melting furnace in which the viscosity is determined, and in which molten glass is added to the forehearth in response to deviations from glass viscosity setpoints. The viscosity in Chrisman is determined using sensed electrical conductivity of the glass flowing through the forehearth. Chrisman also suggests that the viscosity can be determined using a strain gauge on the shaft of the mixer which can be positioned within the forehearth. These solutions proposed by Chrisman involve some uncertainty because of the fact that the glass on which the viscosity is being measured is still within the forehearth. It has been found that measuring viscosity with equipment installed in the mainstream flow of molten glass, such as in the forehearth, is difficult due to the hostile environment within the molten glass for the equipment. The lack of access to the equipment gives the inevitable result that the equipment fails and the measuring process is out of control.

Glass viscosity is one of the major parameters controlling production in the glass industry. Currently, the measurements of glass viscosity discussed above are not being done more than two of three times a day in continuous glass furnaces. This does not provide enough control for preventive actions to correct undesirable viscosities. The viscosity of glass depends on both temperature and composition. Viscosity changes can characterize continuous change in the composition of glass, providing the temperature of the glass in the measuring system is controlled.

There is still a need for a method and apparatus which enables the glass viscosity to be measured on line, and in a continuous mode. It is also important that the viscosity measurement method be accomplished without disturbing the glass manufacturing process. Further, the equipment should be outside of the molten glass in order to give access and longevity to the equipment.

SUMMARY OF THE INVENTION

A method for controlling a glass manufacturing process has now been developed in which an auxiliary stream of molten mineral material, distinct from the streams of material going to the glass forming equipment, is discharged from the molten mineral material delivery means, *the mass flow rate of the auxiliary stream is measured by laser means* and used to determine the viscosity of the molten material. The temperature and the viscosity are used to control the manufacturing process.

This invention provides a method for manufacturing glass comprising feeding molten mineral material from a delivery means through a primary discharge bushing to a means for forming glass. The method then includes the forming glass from the molten mineral material, continuously discharging an auxiliary stream of molten mineral material from the delivery means through an auxiliary discharge outlet, continuously measuring the temperature and continuously measuring by laser means the mass flow rate of the auxiliary stream, calculating the viscosity of the molten mineral material using the measured mass flow rate and temperature, and, optionally, modifying a process parameter in response to the measured temperature of the auxiliary stream and the calculated viscosity of the stream

BRIEF DESCRIPTION OF THE DRAWINGS

FIG. 7 illustrates the electrodes of the glass viscosity controlling device.

FIG. 8a and 8b illustrate the special relationship of the elements of the laser means and the rest of the equipment.

FIGS. 9a, 9b, and 9c illustrate the passage of seeds through a laser beam.

DETAILED DESCRIPTION OF THE INVENTION

Figure 1:
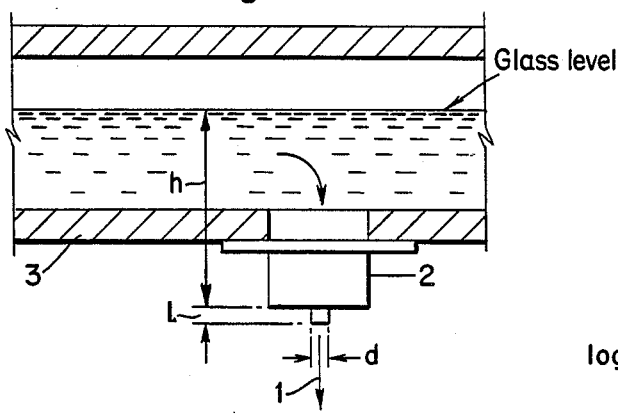
FIG. 1 illustrates a stream of glass exiting glass drain bushing.

The major viscosity-pull relationship is illustrated in Formula 1. This is for a stream 1 of glass exiting from a glass drain bushing 2 installed in channel 3 (see FIG. 1), and is described by formulae 1 and 1' as follows.

$$\mu = n \frac{h \gamma^2 d^4}{Q^1} \qquad 1.$$

or

-continued $$\mu = k \frac{1}{Q} \qquad 1'.$$

where: Q-glass stream pull (lb/hr).

$$k = n \frac{h \gamma^2 d^4}{l} = \text{const}$$

$\mu$=dynamic viscosity (g/cm sec)
h=glass head (in) (see FIG. 1)
$\gamma$=glass density (g/cm$^3$)
d=diameter of bushing opening (in) (see FIG. 1)
l=length of the bushing tip (in) (see FIG. 1)

Figure 2:
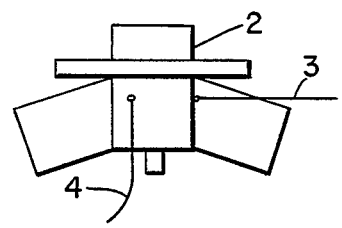
FIG. 2 illustrates glass drain bushing.

A drain bushing 2 is shown on FIG. 2. One can see in FIG. 2 both control thermocouple 3 and glass measurement thermocouple 4. The major formula which is used in this invention can be obtained from formula 1'.

This formula is:

$$\text{Log } \mu = \text{Log } k - \text{Log } Q \qquad 2$$

where: Log k=Log (nh $\gamma^2$d$^4$/l)=const. This is assumed because the temperature of the glass in the bushing is controlled and density does not change significantly. The standard glass used in particular production is described the following way:

$$\text{Log } \mu_o = -a_o + b_o(T_o c_o) \qquad 3$$

Figure 3:
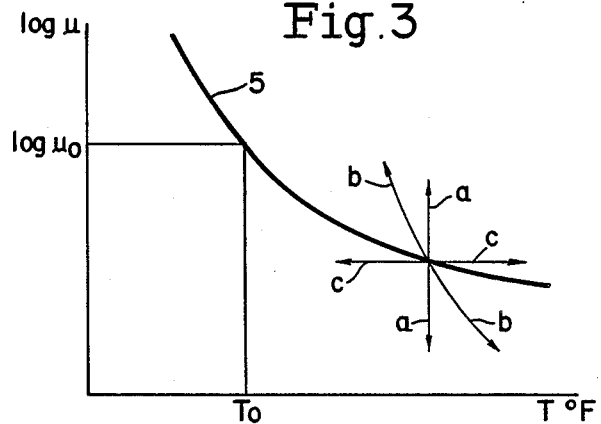
FIG. 3 illustrates the graphic relationship of the variables of equation 3.

Graphically, the equation 3 is depicted in FIG. 3. Changes of the coefficients a, b, c transform the major curve 5 in directions as shown in FIG. 3. It is believed that the major transformation of the base curve can be described by changes of the coefficient "a" in equation 3. In real measurements, the following situation can occur. The viscosity can, for example, drop to Log $\mu_1$, from Log $\mu_o$, under the same T(o), while Log $\mu_1$, is lying on a new curve 6 (see FIG. 4). The curve 7 is a standard curve of Log $\mu_o$=f(T) as described by equation 4 and FIG. 4.

$$\text{Log } \mu_o = -1.296 + 5173/(T(o) - 1023) \qquad 4$$

Figure 4:
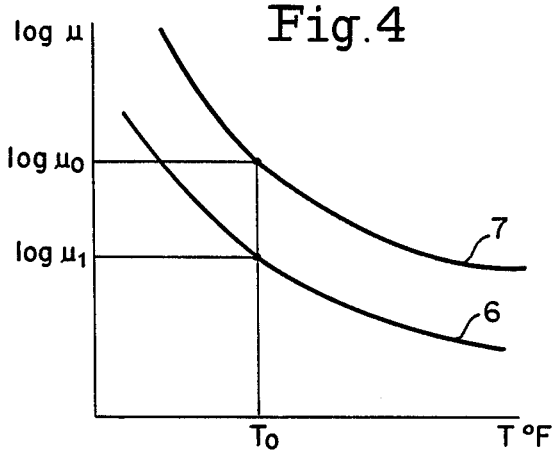
FIG. 4 illustrates the graphic relationship of the variables of equation 4.

According to the above, curve 6 in FIG. 4 has a different coefficient "a" from equation 4, which is equal to −1.296 in formula 4.

The coefficient "a$_o$" for the curve 7 in FIG. 4 can be seen in the following equation 5.

$$\text{curve 7} \quad \text{Log } \mu_0 = -a_0 + \frac{b_0}{T_0 - c_0} = -a_0 + P \text{ or} \qquad 5.$$

$$a_0 = P - \text{Log } \mu_0$$

The equation 6, which describes curve 6, will have coefficient a$_1$.

$$\text{curve 6} \quad \text{Log } \mu_1 = -a_1 + \frac{b_0}{T_0 - c_0} = -a_1 + P \text{ or} \qquad 6.$$

$$a_1 = P - \text{Log } \mu_1$$

Subtracting 5. from 6., one can fine the value a$_1$ (see 7').

$$a_1 - a_0 = -\text{Log } \mu_1 + \text{Log } \mu_0 \qquad 7.$$

-continued

From 7. $a_1 = a_0 - \text{Log } \mu_1 + \text{Log } \mu_0 \qquad 7'.$

From formula 3, one can obtain the corresponding temperature T(o), using formula 8.

$$T_0 = \frac{b_0}{\text{Log } \mu_0 + a_0} + c_0 \qquad 8.$$

Figure 5:
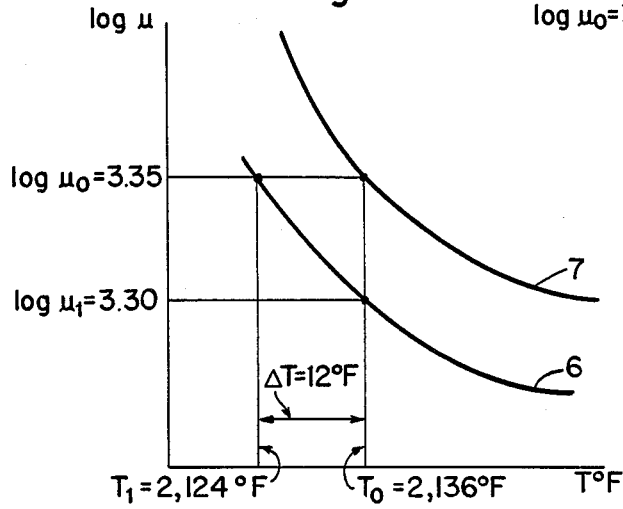
FIG. 5 illustrates the graphic relationship of the variables of equation 4', (curve 7), and curve 6 reflects the viscosity change, while the controlled temperature of the glass strays constant.

Curve 6 can be described by changing a$_o$ to a$_1$ from 7'. To find the temperature T$_1$ on the curve 6, which gives the same Log $\mu_o$=3.35 but on the curve 6, formula 9 and FIG. 5 are used.

$$T_1 = \frac{b_0}{\text{Log } \mu_0 + \underbrace{\text{Log } \mu_0 - \text{Log } \mu_1 + a_0}_{a_1}} + c_o = \qquad 9.$$

$$\frac{b_0}{2 \text{ Log } \mu_0 - \text{Log } \mu_1 + a_0} + c_0$$

The following real example can explain the previous derivations. Curve 7 is described by equation 4'.

$$\text{Log } \mu_0 = -1.296 + \frac{5173}{2136 - 1023} = 3.35 \qquad 4'.$$

In this case, T$_o$ is equal to 2136° F. (see equation 4').

The standard viscosity curve used in this example has Log $\mu_o$=3.35 for T$_o$=2136° F., but the measured real viscosity has Log $\mu_1$=3.30 for the same controlled temperature T$_o$=2136° F. (see FIG. 5). Formula 9 calculates temperature T$_1$, which can provide the same Log $\mu_o$=3.35 viscosity as in the situation when viscosity was on the standard curve 7 but in condition when composition changed. The change in composition is the reason that Log $\mu_o$ viscosity changes from 3.35 to Log $\mu_1$=3.30. The temperature T$_1$, which can still provide necessary production viscosity Log $\mu_o$=3.35 is calculated in equation 10.

$$T_1 = \frac{b_0}{2 \text{ Log } \mu_0 - \text{Log } \mu_1 + a_0} + c_0 = \qquad 10.$$

$$\frac{5173}{2 \cdot 3.35 - 3.3 + 1.296} + 1023 = 2124° \text{ F.}$$

The temperature correction factor is $\Delta T = 2124 - 2136 = -12°$ F. This means that by lowering the glass temperature by 12° F., the viscosity is returned to the same Log $\mu_o$=3.35 under new real glass conditions.

At the same time, one can change the log viscosity by

Figure 6:
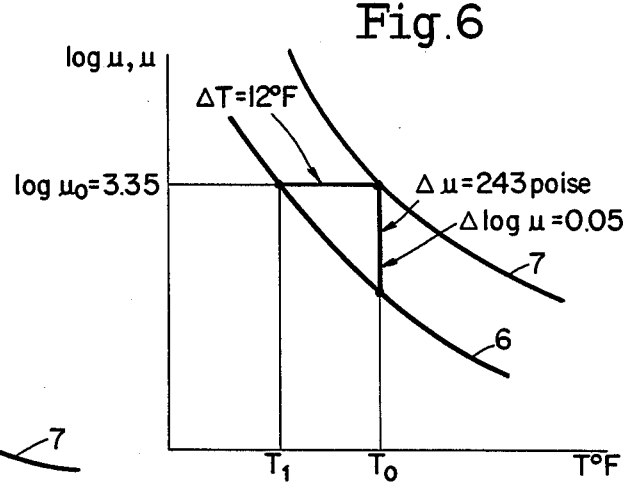
FIG. 6 illustrates the graphic relationship of the correction factors: temperature $\Delta T$, viscosity $\Delta \mu$, and Log $\mu$, $\Delta$Log $\mu$.

Log $\mu$=Log $\mu_o$−Log $\mu_1$=3.35−3.30=0.05—log viscosity correction factor If Log $\mu_o$=3.35, than $\mu_o$=2238 poise.
If Log $\mu_1$=3.30, than $\mu_1$=1995 poise.
Thus, $\Delta \mu = \mu_o - \mu_1 = 2238 - 1995 = 243$ poise—viscosity correction factor.
$\Delta T$=temperature correction factor (°F.)=−12° F.
The results are as follows:
The viscosity is returned to the standard working conditions, to Log $\mu_o$=3.35, by doing one of the following:

1. Decreasing the temperature by 12° F. (see FIGS. 5 & 6);

2. Increasing the viscosity by 243 poise (see FIG. 6);
3. Increase the Log $\mu_1$ by 0.05 (see FIG. 6).

When the viscosity is changed in the traditional manner by changing the main batch, the necessary response for control purposes is not provided. This is because 2 to 3 days are required for complete viscosity change. A fast response can be created to the invention.

The invention installs five to ten feet upstream from the measuring device a system of electrodes as illustrated in FIG. 7. The control system operates such that, when viscosity drops, the power to the electrodes increases, otherwise the power of the electrodes decreases. Such a centralized system does not need to control all the bushings in, for example, fiberglass production, which is suggested in the "mechanical" measuring system of co-pending patent application by Sheinkop and Varrasso, issued as U.S. Pat. No. 4,812,151 on Mar. 14, 1989, herein incorporated by reference. This is possible because of the extreme accuracy of laser-based system of this invention. The laser means of this invention senses very small deviations of viscosity and correspondingly a very small control power change is necessary to maintain the desired glass viscosity.

FIG. 8 depicts the invention schematically. The throughput Q is measured with the help of Neon-Helium laser 11 which sends a collimated beam 12 onto a stream of glass 15.

Figure 10:
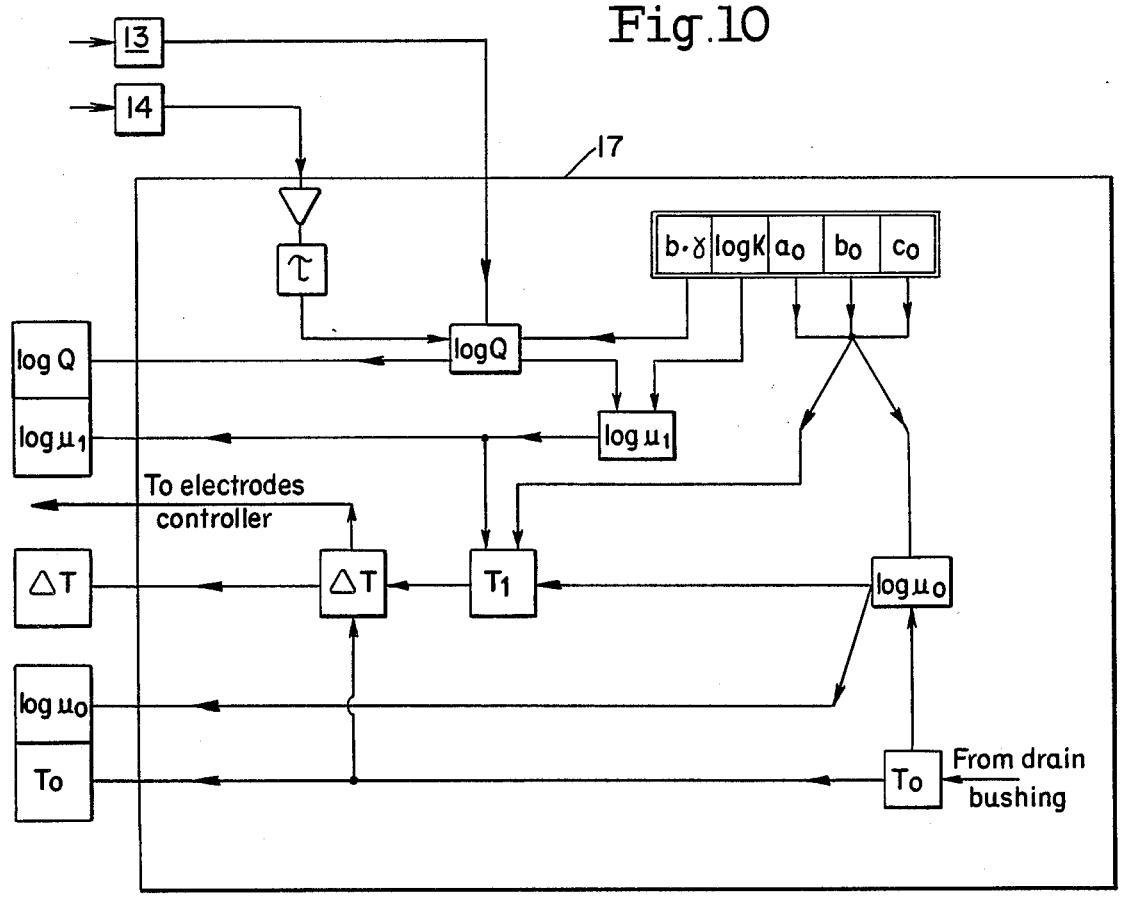
FIG. 10 illustrates the preferred embodiment of the master controller.
Figure 11:
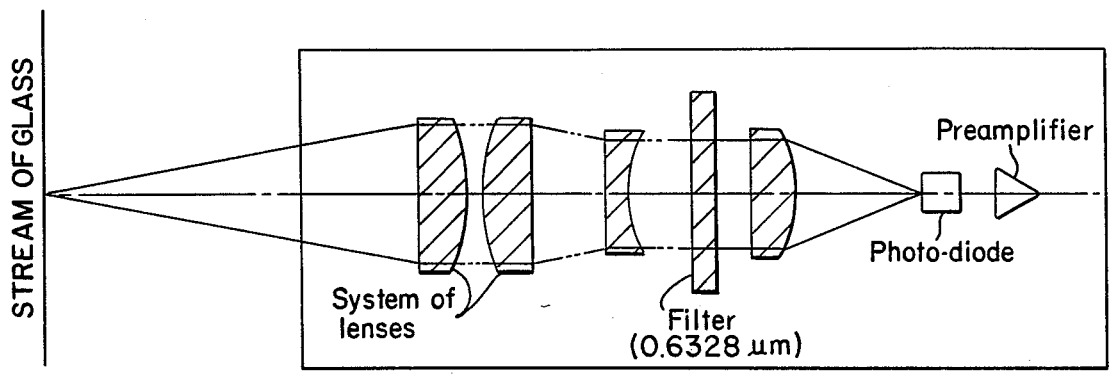
FIG. 11 illustrates the preferred embodiment of the system of lenses.

This reaches the laser dimension sensor 13 and measures the diameter "d" of the glass stream. The signal of the measured diameter "d" is sent to the master controller 17. Details of the small master controller 7 are shown in FIG. 10. The detector 14 desirable has the internal structure of FIG. 11 and is installed, desirably, according to FIG. 8 such that it continuously picks up the reflection of the seeds or air bubbles in the molten glass. These seeds are always existing in the molten glass. The seeds cross the beam of the laser means. The laser beam is many times larger than the diameter of a seed. The power of reflection depends on the process of a seed's passage through the beam as shown in FIGS. 9a, 9b, and 9c. FIG. 8 has the following parts: helium-neon laser 11, collimated beam 12, laser dimension sensor 13, velocity detector 14, stream of glass 15, glass drain bushing 16, master controller 17, electrode system 18, and glass channel 19.

The primary components of the laser means of FIG. 8 are commercially available. For example, the laser dimension sensor 13 is manufactured by Tygo Corporation, Laurel Brook Road, Middlefield, Conn. 06455. The other laser means are commercially available from the Wyko FIG. 9a illustrates that as soon as the signal from the reflection appears or, when the seen just starts to cross the beam, the clock starts. FIG. 9b illustrates the seed inside the beam and the signal reaching the maximum power and staying the same for the duration of travel inside the beam. FIG. 9c illustrates that as soon as the power or reflection starts to drop, the seed begins to pass the beam, the clock stops. Thus, as can be seen from the situation in FIG. 9a to the situation in FIG. 9c, the seed passes the distance equal to the diameter of the beam b and the corresponding time $\tau$ is recorded by the clock.

FIG. 10 schematically depicts a major flow of signals in the master controller providing calculations necessary for obtaining control parameters $\Delta T$ and continuous knowledge of the glass viscosity values. It is not individual values, but average values collected for about five minutes that are used and displayed. This time can vary.

Position 13 in FIG. 10 continuously delivers values of the stream diameter d. At the same time using the data from detector 14, the clock in position $\tau$ delivers times $\tau$, necessary for a seed to cross the eliminating beam, to position Log Q. In position memory in FIG. 10, $b \times \gamma$, Log k, $a_o$, $b_o$, $c_o$ are stored. In position Log Q, the following calculation is performed using equation 11.

$$\text{Log } Q = \text{Log } 0.785 \cdot d^2 \cdot b \cdot \gamma / \tau \qquad 11$$

Where: $b \times \gamma$ is taken from memory.
b = diameter of the colimated beam
$\gamma$ = glass density Calculated Log Q is send to the position Log $\mu_1$. To calculate Log $\mu_1$, the real viscosity of the glass, Log k is taken from memory and equation 12 is used (presented above in formula 2)

$$\text{Log } \mu_1 = \text{Log } k - \text{Log } Q \qquad 12$$

Parallel to the described flow of signals, the other flow of signals takes place. The glass temperature in the drain bushing $T_o$ is sent to the master controller, position $T_o$, and after this to position Log $\mu_o$, the control viscosity which is correct only if the glass composition does not change. At this time, Log $\mu_o$ is calculated using equation 13, while $a_o$, $b_o$, $c_o$ are sent from the storage to position Log $\mu_o$ as well (presented above in formula 3).

The Log $\mu_o$ is sent to position $T_1$, while Log $\mu_1$, $a_o$, $b_o$, $c_o$ are also sent to the position $T_1$. $T_1$ is calculated using the equation 14 (derived by formula 9).

$$T_1 = b_o/(2 \text{ Log } \mu_o - \text{Log } \mu_1 + a_o) + c_o \qquad 14$$

After the parameter $T_1$ is calculated, the temperature correction factor $\Delta T$ is calculated in position $\Delta T$ using the equation 15.

$$\Delta T = \pm (T_1 - T_o) \qquad 15$$

This temperature correction factor $\Delta T$ is simultaneously sent to the output of the system and to the glass temperature controller of electrodes.

If $\Delta T$ is negative, the signal is sent to the electrodes to decrease the temperature of the glass or vice versa. If $\Delta T = 0$ or smaller than $\Delta T_{min}$, no control is activated. The invention provides the following advantages. The invention is a laser-based or laser-operated system given significantly more accurate results than possible in the past. The invention registers the change of viscosity very fast, thus much faster corrective action to viscosity changes can be performed in glass manufacturing. The invention has no moving mechanical parts as it is in U.S. Pat. No. 4,812,151, which is given as a reference in this application, increases its reliability of the invention. The invention provides an economical viscosity control having greater accuracy because of the absence of moving, mechanical parts thus allowing a centralized viscosity control station.

I claim:
1. A method of manufacturing glass comprising:
   feeding molten mineral material from a delivery means through a primary discharge bushing to a means for forming mineral fibers;
   forming glass from the molten mineral material;

discharging continuously an auxiliary stream of molten mineral material from the delivery means through an auxiliary discharge outlet;

measuring continuously temperature and mass flow rate by a laser means of the auxiliary stream;

calculating viscosity of the molten mineral material using the laser measured mass flow rate; and modifying, as needed, a process parameter in response to the measured temperature of the auxiliary stream and the calculated viscosity of the stream.

2. The method of claim 1 wherein said modifying said process parameter comprises changing the composition of the batch material being supplied to the furnace.

3. The method of claim 1 wherein said modifying said process parameter comprises changing the temperature of the molten material being discharged through the primary discharge bushing.

4. The method of claim 3 wherein said modifying said process parameter comprises changing the temperature of a channel positioned between the primary discharge bushing and the furnace.

5. A means for monitoring viscosity of molten glass comprising:

a laser means, said laser means projects a collimated beam;

a laser dimension sensor, said laser dimension sensor detects the diameter of an auxiliary stream;

a velocity detector means, said velocity detector means detects a velocity of a seed in a stream of molten glass as said seed passes through said collimated beam; and a control means, said control means calculates a viscosity of said molten glass by using said diameter and said velocity.

6. The means of claim 5 wherein said control means alters a condition of said molten glass.

7. The means of claim 6 wherein said altered condition of said molten glass is temperature upstream to said auxiliary stream.

* * * * *